United States Patent
Klein

(12) United States Patent (10) Patent No.: US 8,249,214 B2
Klein (45) Date of Patent: Aug. 21, 2012

(54) DEVICE FOR THE ONLINE DETERMINATION OF THE CONTENTS OF A SUBSTANCE, AND METHOD FOR USING SUCH A DEVICE

(75) Inventor: Albert Klein, Simmersfeld (DE)

(73) Assignee: Elisabeth Katz, Simmersfeld (DE)

( * ) Notice: Subject to any disclaimer, the term of this patent is extended or adjusted under 35 U.S.C. 154(b) by 151 days.

(21) Appl. No.: 12/734,316

(22) PCT Filed: Oct. 23, 2008

(86) PCT No.: PCT/EP2008/008980
§ 371 (c)(1),
(2), (4) Date: Apr. 23, 2010

(87) PCT Pub. No.: WO2009/053073
PCT Pub. Date: Apr. 30, 2009

(65) Prior Publication Data
US 2010/0232569 A1  Sep. 16, 2010

(30) Foreign Application Priority Data
Oct. 24, 2007 (DE) .......................... 10 2007 051 135

(51) Int. Cl.
*G01N 23/06* (2006.01)
(52) U.S. Cl. .......................................... 378/53
(58) Field of Classification Search .................... 378/51, 378/53, 54, 57, 58, 70
See application file for complete search history.

(56) References Cited

U.S. PATENT DOCUMENTS

| 3,052,353 A | 9/1962 | Pritchett |
| 4,259,577 A * | 3/1981 | Jakosky et el. ................. 378/55 |
| 4,359,639 A | 11/1982 | Wykes et al. |

FOREIGN PATENT DOCUMENTS

| DE | 54508 A1 | 3/1967 |
| DE | 214 931 A1 | 10/1984 |
| DE | 37 35 749 A1 | 5/1988 |
| DE | 265 696 A1 | 3/1989 |
| DE | 198 24 039 A1 | 12/1999 |
| DE | 10 2005 020 567 A1 | 11/2006 |
| FR | 1476433 A | 4/1967 |
| GB | 2 046 435 A | 11/1980 |
| GB | 2 066 456 A | 7/1981 |
| SU | 939 086 A1 | 6/1982 |
| SU | 1183875 A * | 10/1985 |

* cited by examiner

*Primary Examiner* — Irakli Kiknadze
(74) *Attorney, Agent, or Firm* — Rabin & Berdo, P.C.

(57) ABSTRACT

A device for the online determination of the contents of a substance having a gamma-radiating isotope, which includes at least one detector, which measures the natural gamma radiation of said isotope. In order to be able to easily calibrate the device, a measurement is carried out at the same location for determining the surface dimensions of the substance within the detection region of the detector or of a representative partial region.

19 Claims, 3 Drawing Sheets

Figure 1:
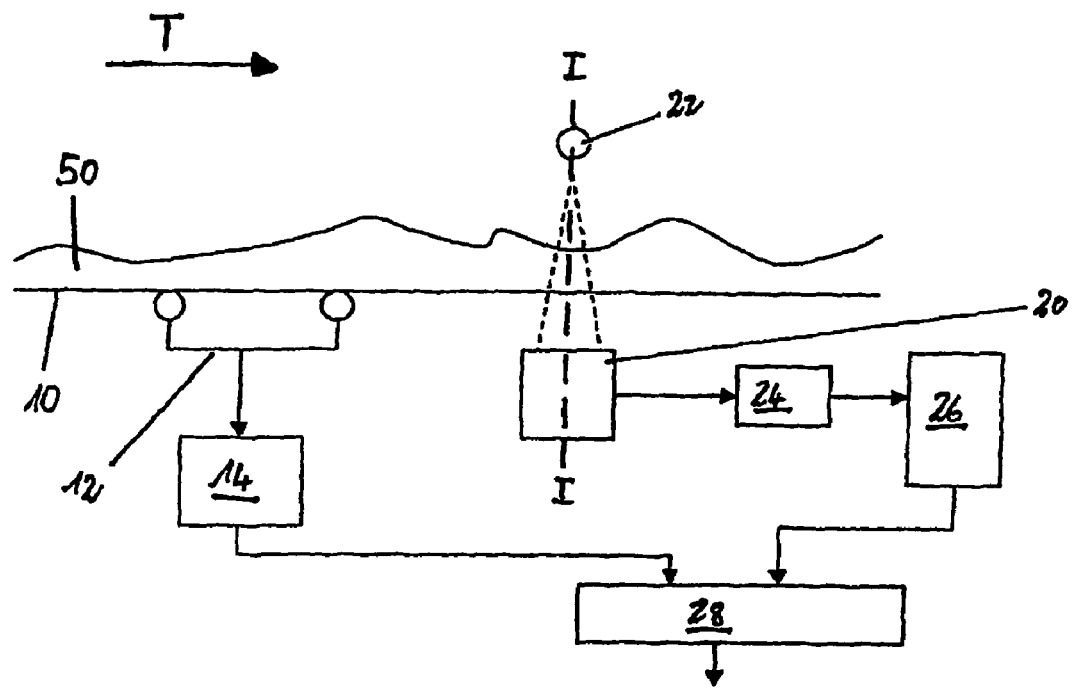

DEVICE FOR THE ONLINE DETERMINATION OF THE CONTENTS OF A SUBSTANCE, AND METHOD FOR USING SUCH A DEVICE

TECHNICAL FIELD OF THE INVENTION

In the field of industrial measuring technology, the natural gamma radiation of a substance is measured in order to determine different material parameters of this substance.

In particular, this method is used for determining the ash content of coal and for determining the potassium content of potassium salt. The potassium content is measured by determining the concentration of the radioactive isotope K-40 which is present worldwide in the same concentration in potassium. The ash content is measured by determining additional radioactive isotopes that are contained in the ash.

With a sufficiently large measuring volume, meaning if the measuring depth is sufficient so that saturation occurs, only a large-surface detector or a detector array is needed for detecting a statistically backed number of events during a suitable time period, so that the desired measuring variables can be determined following a corresponding calibration. This is generally the case if the detector is mounted on an industrial bunker for example.

In many cases, however, it is desirable to carry out a measurement on material conveyed on conveying belts or under different measuring conditions where the so-called saturation layer thickness is not reached. In those cases, either the layer thickness must be kept constant or a compensation of the layer thickness or in general of the available measuring volume is required.

PRIOR ART

Most widely used is the technique of carrying out a measurement with material on conveying belts. Belt scales are primarily used to compensate for the belt occupancy or bulk material level, wherein radiometric as well as mechanical belt scales are used. These units either exist already when the device for determining the concentration is installed, since the determination of the mass flow is of general interest, or they are installed at the same time as the measuring device. With radiometric belt scales the detector for determining the natural gamma radiation is installed at a far enough distance to the radiation sources on the belt scale that the measuring of the natural gamma radiation is not disturbed by these radioactive sources. With mechanical belt scales, the belt section determined for realizing the measurement in most cases is noticeably larger than the section determined by the detector for the natural gamma radiation. As a result, static calibrations (calibrations made while the belt is stopped and using mostly previously analyzed samples) are often very difficult and involved and frequently not very precise. Either large numbers of samples are required or the sample must be displaced without changing the mass per unit area and without changing the shape or the cross-sectional profile of the sample. In practical operations, this is achieved by manually moving the conveying belt on which the sample for calibration is positioned—oftentimes weighing more than a hundred kilograms—so that the sample is displaced between belt scale and radiation detector. With dynamic measurements, meaning for measurements taken while the belt is moving and under conditions similar to operational conditions, this problem does not occur, to be sure, but large amounts of sample material must be tested which is also extremely involved and subject to errors.

Subject Matter of the Invention

It is the object of the present invention to create a device which makes possible a static calibration, using a comparably small sample, wherein this sample is not displaced during the calibration.

This object is solved with a device having the features as disclosed in claim 1.

According to the invention, the measuring of the natural gamma radiation and the measuring of the mass per unit area are realized at the same location. If a mechanical belt scale is used for determining the mass per unit area, then it must either be ensured that the radiation detector or detectors used detect the total region of the substance for which the weight is detected by the mechanical belt scale, or it must be ensured that the region detected by the detector is representative of the substance measured by the belt scale.

According to one preferred embodiment disclosed in claim 2, the mass per unit area are determined with the aid of a gamma or X-ray radiator which irradiates the substance, wherein the radiation transmitted through the substance at least in part impinges on the detector for measuring the natural radioactivity, so that this detector functions to measure the natural radioactivity of the sample as well as to measure the weakening of the irradiated radiation and thus can be used to determine the mass per unit area. However, this requires means for distinguishing between the intensity of the gamma radiation of the isotope, measured by the detector, and the intensity of the transmitted radiation, wherein this can be achieved in two different ways:

On the one hand it is possible to use a detector having a sufficient energy resolution. The at least one additional radioactive radiator emits energy quanta with energies that differ strongly enough from the energies of the natural radioactive radiation, so that during a simultaneous detection the natural gamma radiation can be separated from the radiation emitted by the nuclide/X-ray tube or tubes. For the purpose of evaluation, a multi-channel analyzer is installed downstream of the detector which detects the spectrum of the occurring radiation. The natural radiation and the radiation caused by the nuclide/X-ray tube can thus be separated in a single evaluation unit and the concentration of the compensated for occupation level can be computed. Suitable nuclides are, in particular, cobalt, americium and cesium.

If the natural gamma radiation is limited to a few spectral lines, the multi-channel analyzer can also be replaced by a sufficient number of discriminators which make it possible to separate the spectral lines and the dragging of pulses to the low-energy range which is essentially caused by the Compton Effect.

According to claim 8, separating the signals coming from the individual radiators and the natural gamma radiation can also be achieved through alternately fading out the radiation from the nuclide/X-ray tube, wherein a chopped operation is especially advantageous (claim 9).

According to claim 18, the device according to the invention is particularly suitable for determining the potassium content in potassium salt and, according to claim 20, for determining the ash content in coal.

Further advantageous embodiments are disclosed in the additional dependent claims.

SHORT DESCRIPTION OF THE DRAWINGS

Shown are in

Figure 2:
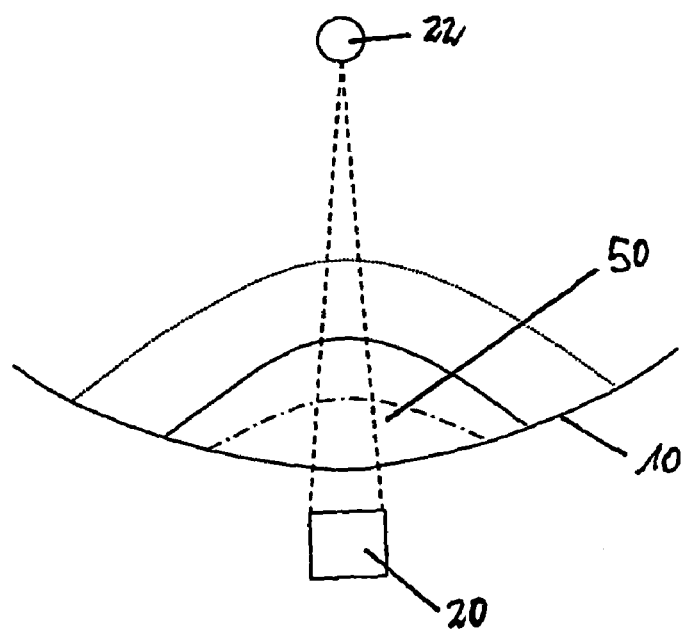
Figure 3:
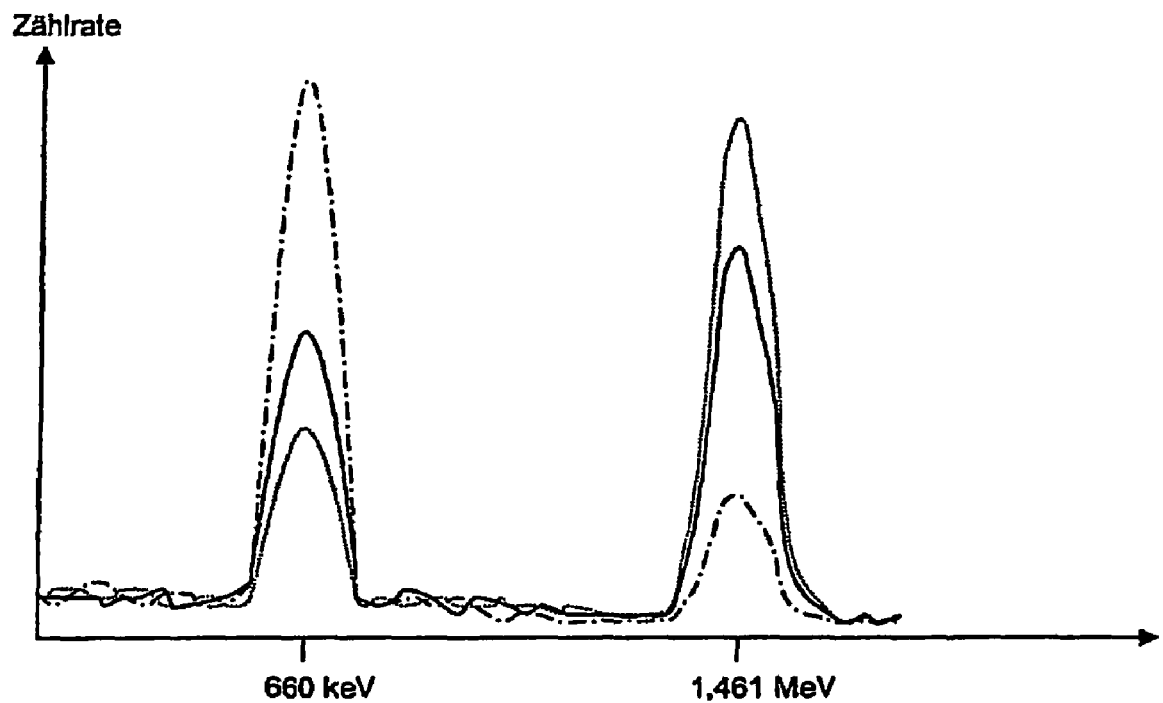
Figure 4:
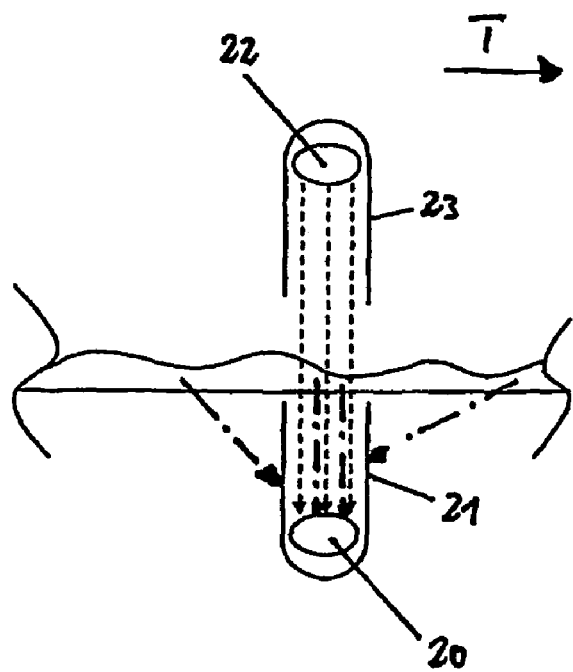
Figure 5:
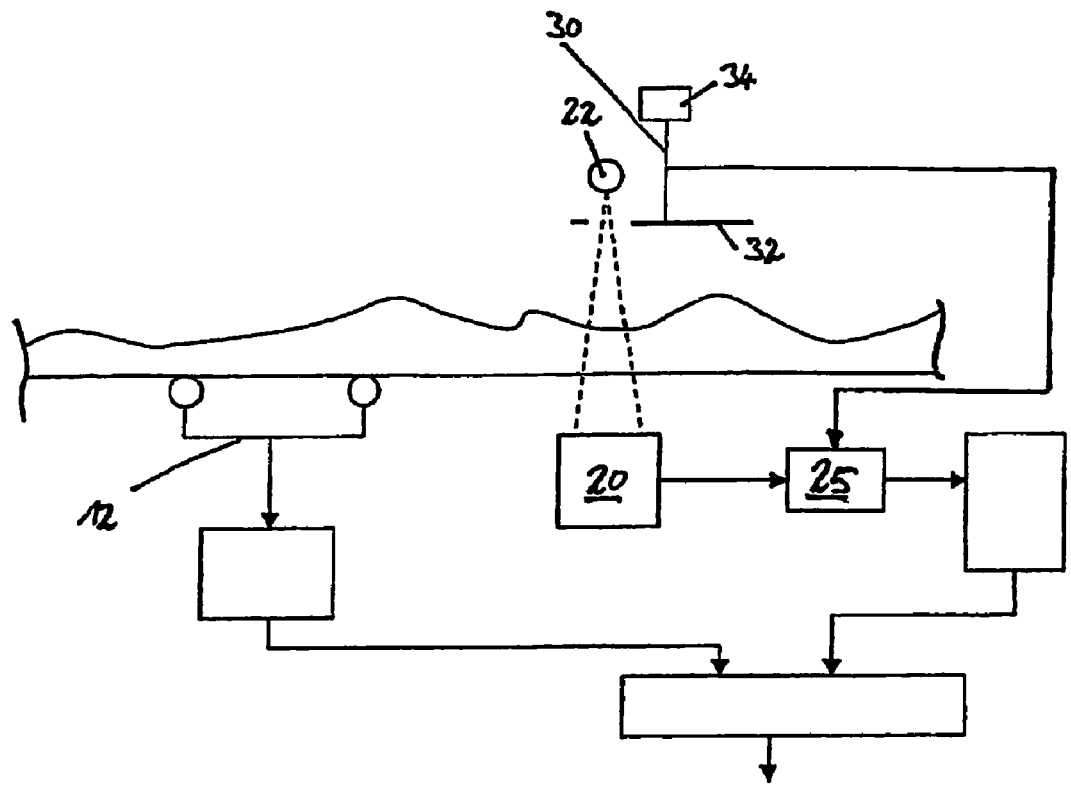
Figure 6:
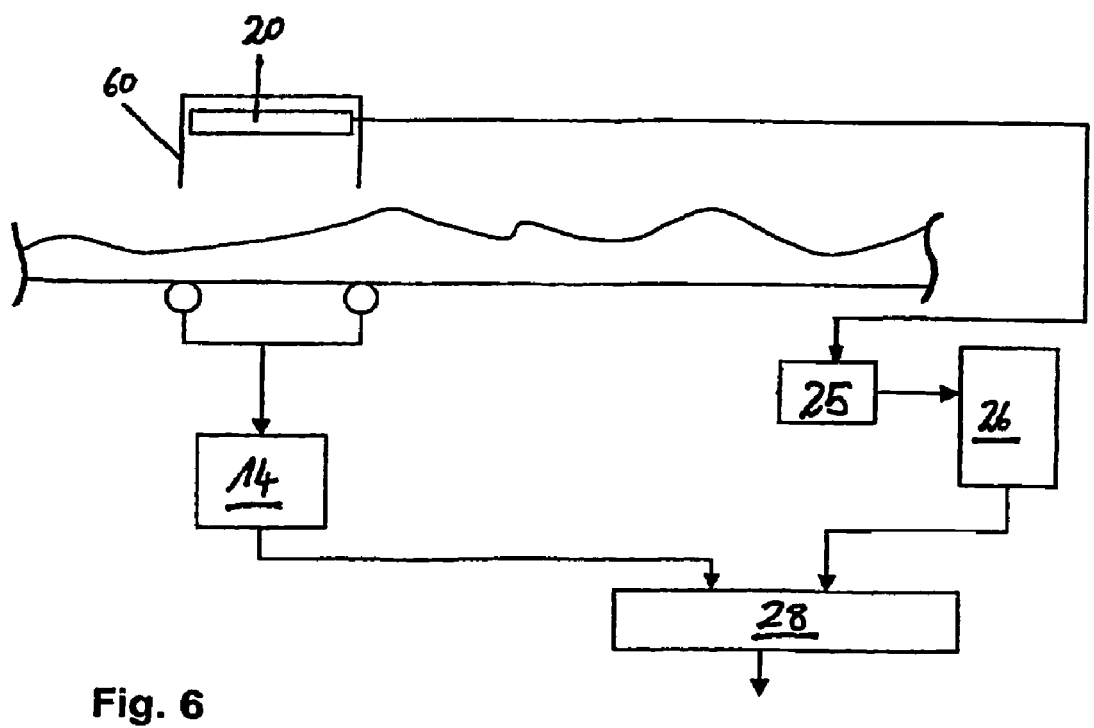

FIG. 1 A schematic representation of a first embodiment of the invention;

FIG. 2 A cross section along the line I-I in FIG. 1, also shown as a schematic representation, wherein different substance levels are drawn in;

FIG. 3 Typical spectra for different substance amounts;

FIG. 4 The measuring range if two collimators are present, shown schematically;

FIG. 5 A second example for the first embodiment, shown in a schematic representation; and FIG. 6 A second embodiment of the invention.

DESCRIPTION OF THE PREFERRED EMBODIMENTS

FIG. 1 shows a first example of a first embodiment of the invention in the form of a strongly diagrammatic view. The device shown herein is used to determine the total amount of potassium conveyed on a conveying belt 10, wherein potassium salt 50 is conveyed on the belt 10 in the direction T. The goal is to use the shown device for determining the total amount of potassium that is conveyed per time unit. The device is provided for this with a mechanical belt scale 12 and a corresponding evaluation unit 14. The mechanical belt scale 12 with the evaluation unit 14 functions to determine the total tonnage of the potassium salt. Since the share of potassium in the potassium salt can vary, it is not possible to immediately draw a conclusion relating to the share of the potassium tonnage in the total tonnage. A measuring device is therefore provided which determines the percentage share of the potassium in the potassium salt.

This measuring device comprises a cesium 137 source 22 which for this example is arranged above the conveyor belt 10, as well as a detector 20 that is arranged below the conveyor belt 10. The detector can be a NaJ detector, for example. The measuring device furthermore comprises a multi-channel analyzer 24, arranged downstream of the detector 20, as well as a measuring computer 26 for evaluating the signals from the multi-channel analyzer 24. The output of the evaluation unit for the belt scale 14 and the output of the measuring computer 26 are connected to a display unit 28 which displays and issues the desired information, for example the total tonnage per hour of potassium salt, as well as the total tonnage per hour of potassium.

The mode of operation of the measuring device is now explained in further detail with reference to FIGS. 1 to 3, wherein FIG. 2 shows a section through the conveyor belt, at the location of the measuring device, and wherein different filling levels of the potassium salt are plotted on at the conveyor belt 10. The dotted line in this case shows the maximum level of the bulk material, the drawn-out line shows the average level of the bulk material and the dash-dot line shows a low level. The cesium 137 source 22 irradiates at least a portion of the potassium salt flow transported on the conveyor belt 10, wherein the geometry is arranged such that the total radiation transmitted through the potassium salt impinges on the detector 20. The gamma quanta radiated by the cesium 137 source 22 have an energy of 660 eV, so that the absorption of this radiation depends in a manner known per se on the irradiated amount of the substance, namely on the mass per unit area.

In addition to the radiation from the cesium 137 source 22—if applicable transmitted through the potassium salt—the natural radiation of the potassium isotope K-40 also impinges onto the detector 20 with a quantum energy of 1,461 MeV. The maximum filling level of the potassium salt is such that it does not result either in an almost complete absorption of the 660 KeV radiation or in a saturation of the natural gamma radiation of the K40. Spectra such as the one shown with the example in FIG. 3 are consequently obtained for the various bulk material levels.

With a low bulk material filling level (dash-dot line), the absorption of Cs-137 radiation is low and the signal intensity measured by the detector 20 is high. The signal intensity of the natural K-40 radiation at 1,461 MeV is correspondingly low. If the level is increased with the same composition of the irradiated substance, then the peak at 660 keV is correspondingly reduced while the peak at 1,461 MeV is increased accordingly. The continuous line shows the spectrum for the average bulk material level while the dotted line shows the spectrum for the high level.

If we consider the dependence of the counting rate for the K-40 radiation in dependence on the layer thickness in a linear approximation, the following ratio is obtained:

$$\frac{F_{K-40-peak}}{\ln\frac{F_{Cs-137-peak}}{F_{empty}}} = \text{const}\,(concentration_{K-40})$$

wherein:

$F_{K-40-peak}$=area below the K-40-peak $F_{Cs-137-peak}$=area below the Cs-137-peak $F_{empty}$=area below the Cs-137 peak when the conveyor belt is empty const(concentration$_{K-40}$)=constant which depends only on the K-40 concentration with the given geometry.

This approach could be called a "semi-linear" approach, which can be used if a simple measuring geometry can be realized with the aid of strong collimation and if the maximum observed bulk material level is not very high.

The areas below the peaks and the corresponding quotients can be determined directly, so that with a change in the quotient, we can directly deduce a change in the K-40 and thus in the potassium content. The dependence of const(concentration$_{K-40}$) on the K-40 concentration in many cases can be seen as linear.

To achieve a higher accuracy, it must for the most part be taken into consideration that the counting rate for the K-40 signal does not increase linear with the occupancy since the layer close to the detector absorbs photons from the layer at a distance to the detector. With extremely high layer thicknesses, saturation occurs and the above-described approximation method can no longer be used. It must furthermore be taken into consideration that with an increase in the layer thickness, the volume used for the potassium measurement does not increase linear, but increases faster because more radiation also impinges from the side onto the detector. The detected volume therefore does not take the form of a cylinder, but rather that of a cone. The opening angle can be defined by a collimator. The algorithms required for the evaluation are known and are used at the present time with potassium belt scales, for example, or with ash content measuring devices which are based on the measurement of natural gamma radiation.

In practical operations, corresponding calibration curves will be generated by taking measurements at differently high bulk material levels. The calibration is not very involved, however, since on the one hand only a relatively small amount of material is needed and, on the other hand, the conveyor belt need not be operational. The static calibration makes it possible to easily measure a sample at different layer thicknesses (bulk material levels).

The calibration and the mathematical treatment are simplified considerably if the irradiated region of the substance, which is "seen" by the detector 20, is identical to the region of the substance, the K-40 radiation of which impinges on the detector 20. An upper and a lower collimator 23, 21 can be provided (FIG. 4) for this, wherein these collimators define the viewed spatial region. In particular the lower collimator 21 is of considerable importance since otherwise K-40 radiation of a substance that is not located in the region irradiated by the cesium 137 source 22 is also measured and the transmitted radiation of this substance also impinges on the detector 20. The lower collimator should essentially be impenetrable for the 1,461 MeV radiation and preferably consists of lead.

A spectrum such as the one shown in FIG. 3 is generated by the multi-channel analyzer 24 and is evaluated with the known algorithms by the measuring computer 26. Since the two peaks are positioned at a long distance to each other, it would also be possible to replace the multi-channel analyzer 24 with a discriminator circuit.

FIG. 5 shows a second example for the first embodiment of the invention which can be operated without multi-channel analyzer or discriminator circuit. The measuring principle is basically the same as described in the above because the peaks are analyzed at 660 keV and 1,461 MeV. To determine in that case which pulses measured by the detector 20 come from which radiation source, so as to distinguish between them, a radiation chopper 30 is arranged above the conveyor belt 10 in the radiation path for the Cs-137 source 22, wherein this chopper consists of a aperture wheel 32 and a motor 34. The signals from the detector 20 are conducted to a pulse counter 25 which is synchronized by the radiation chopper 30, so that the pulse counter 25 "knows" which counted pulses belong to the 660 keV peak and which pulses belong to the sum of the 660 keV and the 1,461 MeV peak. The difference must first be computed during the evaluation, so as to obtain separate "counting rates" for the two energies. The mathematical evaluation corresponds to the one described in the above.

FIG. 6 schematically shows a second embodiment of the invention. As explained in the above, the measuring of the absorption of the radiation coming from the cesium 137 source 22 is used to determine the weight of the potassium salt in the measuring region, meaning the belt occupancy over a specific belt section. Of course, this information can in principle also be obtained via the mechanical belt scale. However, it must be considered in that case that the viewed amount of the substance is relatively large. Ideally, the same region is used for measuring the weight with the belt scale and for measuring the natural K-40 radiation, as indicated schematically in FIG. 6. Here too, the measuring range is determined with the aid of a collimator 60. One disadvantage of the second embodiment, as compared to the first embodiment, is that considerably larger amounts of the potassium salt are needed for the calibration.

A surface scanner can alternatively be used for compensating the bulk material level, wherein this scanner measures the profile of the conveyed potassium salt on the conveyor belt at the location where the K-40 radiation is determined. With the assumption of a constant density, the weight can be computed once the profile that is "seen" by the detector 20 is known, so that a corresponding compensation of the occupancy level is possible in that case as well. A surface scanner of this type, for example, can operate with lasers.

The present invention was shown with the aid of a determination of the amount of potassium in a potassium salt. However, this method can in principle also be used for other substances as long as these have isotopes emitting gamma rays with a suitable wavelength for which it is ensured that the isotope distribution is constant and known.

REFERENCE NUMBER LIST 10 conveyor belt
12 mechanical belt scale
14 evaluation unit for the belt scale
20 detector
21 lower collimator
22 Cs-137 source
23 upper collimator
24 multi-channel analyzer
25 pulse counter
26 measuring computer
28 output unit
30 chopper
32 aperture wheel
34 motor
50 potassium salt
60 collimator

The invention claimed is:

1. A device for the online determination of the content of a substance having a gamma-radiating isotope, wherein the device comprises:
    at least one detector, positioned at a location, which measures the natural gamma-radiation of the isotope, the device carrying out at the location a measurement for determining the mass per unit area of the substance in a detection region of the detector or in a representative partial region;
    a gamma or X-ray radiator for irradiating the substance, at least a portion of the radiation passing through the substance impinging on the detector so that the detector measures the radiation that passes through; and
    means for differentiating between the intensity measured by the detector for the natural gamma radiation of the isotope and that of the transmitted radiation.

2. The device according to claim 1, wherein the gamma or X-ray radiator is an americium, cesium or cobalt radiator.

3. The device according to claim 1, wherein the gamma or X-ray radiator is an X-ray tube.

4. The device according to claim 1, wherein the detection region for the at least one detector is delimited by at least one collimator.

5. The device according to claim 1, wherein the means for differentiating comprises a multi-channel analyzer that is arranged downstream of the detector.

6. The device according to claim 1, wherein the means for differentiating comprises a discriminator, arranged downstream of the detector, for realizing thresholds or windows.

7. The device according to claim 1, wherein the means for differentiating comprises a radiation chopper that is arranged between the gamma or X-ray radiator and the substance.

8. The device according to claim 7, wherein the radiation chopper operates with clocked timing.

9. The device according to claim 1, wherein the substance is transported with the aid of a conveying means through the measuring device.

10. The device according to claim 9, wherein the substance flow is conveyed on a conveyor belt that is the conveying means.

11. The device according to claim 9, further comprising a device for measuring the mass flow of the substance.

12. The device according to claim 11, wherein the device for measuring the mass flow is a mechanical belt scale.

13. The device according to claim 11, wherein the device for measuring the mass flow is a radiometric belt scale.

14. The device according to claim 1, wherein the mass per unit area is determined with the aid of at least one distance sensor and assuming a constant density of the substance.

15. The device according to claim 14, wherein the material flow of the substance is determined by additionally measuring the material speed.

16. A method of using a device according to claim 1, wherein the substance to be measured contains potassium and that the concentration of the radioactive isotope K-40 is determined.

17. A method using a device according to claim 1, wherein the substance to be measured is coal and that the natural gamma radiation is used for determining the ash content and, in combination with a mass flow measurement, a conveyed amount of ash and ash content of a batch.

18. A device for the online determination of the content of a substance having a gamma-radiating isotope, wherein the device comprises:
   at least one detector, positioned at a location, which measures the natural gamma-radiation of the isotope, the device carrying out at the location a measurement for determining the mass per unit area of the substance in a detection region of the detector or in a representative partial region;
   a gamma or X-ray radiator for irradiating the substance, at least a portion of the radiation passing through the substance impinging on the detector so that the detector measures the radiation passing through; and
   means for differentiating between the intensity measured by the detector for the natural gamma radiation of the isotope and that of the transmitted radiation,
   wherein a transport means, that transports the substance through the device, is irradiated by the gamma or X-ray radiator.

19. A method of using a device for the online determination of the content of a substance having a gamma-radiating isotope containing potassium, the device including at least one detector positioned at a location, the method comprising:
   measuring the natural gamma-radiation of the isotope with the at least one detector;
   carrying out a measurement, at the location and with the device, for determining the mass per unit area of the substance in a detection region of the detector or in a representative partial region;
   determining the concentration of the radioactive isotope K-40 in the substance;
   determining a mass flow measurement, potassium conveying rate and potassium conveyed during a specific time period; and
   determining the potassium content from the K40-concentration and, in combination with the mass flow measurement, the potassium conveying rate and the potassium conveyed during the specific time period.

* * * * *